US010743945B2

(12) United States Patent
Penenberg

(10) Patent No.: US 10,743,945 B2
(45) Date of Patent: Aug. 18, 2020

(54) SURGICAL METHOD AND WORKFLOW

(71) Applicant: Radlink, Inc., El Segundo, CA (US)

(72) Inventor: Brad L. Penenberg, Los Angeles, CA (US)

(*) Notice: Subject to any disclaimer, the term of this patent is extended or adjusted under 35 U.S.C. 154(b) by 0 days.

(21) Appl. No.: 15/133,999

(22) Filed: Apr. 20, 2016

(65) Prior Publication Data

US 2016/0287345 A1    Oct. 6, 2016

Related U.S. Application Data

(63) Continuation-in-part of application No. 14/481,810, filed on Sep. 9, 2014, which is a continuation-in-part of application No. 13/633,799, filed on Oct. 2, 2012, now Pat. No. 8,831,324.

(51) Int. Cl.
| | |
|---|---|
| A61B 6/00 | (2006.01) |
| A61B 34/00 | (2016.01) |
| G16H 40/63 | (2018.01) |
| G06F 19/00 | (2018.01) |
| A61B 6/12 | (2006.01) |
| A61B 90/00 | (2016.01) |

(52) U.S. Cl.
CPC ............. *A61B 34/25* (2016.02); *A61B 6/12* (2013.01); *A61B 6/465* (2013.01); *A61B 6/467* (2013.01); *A61B 6/468* (2013.01); *A61B 6/505* (2013.01); *A61B 6/5258* (2013.01); *A61B 6/5294* (2013.01); *A61B 6/563* (2013.01); *A61B 6/587* (2013.01); *G06F 19/321* (2013.01); *G06F 19/3481* (2013.01); *G16H 40/63* (2018.01); *A61B 2034/252* (2016.02); *A61B 2034/254* (2016.02); *A61B 2034/256* (2016.02); *A61B 2090/376* (2016.02)

(58) Field of Classification Search
CPC ......... A61B 34/25; A61B 6/468; A61B 6/563; A61B 6/12; A61B 6/4441; A61B 6/5241; A61B 6/5258; A61F 2/4657; A61F 2/34; A61F 2/4609; G06F 19/321; G06F 19/3406; G06F 19/3481
See application file for complete search history.

(56) References Cited

U.S. PATENT DOCUMENTS

| | | |
|---|---|---|
| 5,862,249 A | 1/1999 | Jang et al. |
| 6,458,081 B1 | 10/2002 | Matsui et al. |
| 7,783,008 B2 | 8/2010 | Jabri |

(Continued)

OTHER PUBLICATIONS

Jones et al., "Measuring Angles on Digitalized Radiographic Images Using Microsoft PowerPoint" West Indian Med J 2008, 57 (1): 14-19.*

(Continued)

*Primary Examiner* — Katherine L Fernandez
*Assistant Examiner* — Colin T. Sakamoto
(74) *Attorney, Agent, or Firm* — Cislo & Thomas, LLP; Kelly W. Cunningham

(57) ABSTRACT

A surgical method and workflow to improve the efficiency of a surgical procedure by intraoperatively acquiring a digital radiographic image, processing the digital radiographic image, and using information based on the radiographic image to make adjustments during the surgical procedure. A checklist of parameters may be displayed so that the surgeon can confirm all considerations have been made for the surgical procedure.

29 Claims, 9 Drawing Sheets

(56) References Cited

U.S. PATENT DOCUMENTS

| | | | |
|---|---|---|---|
| 8,369,593 | B2 | 2/2013 | Peng et al. |
| 8,611,697 | B2 | 12/2013 | Nathaniel et al. |
| 9,109,998 | B2 | 8/2015 | Nathaniel et al. |
| 9,111,180 | B2 | 8/2015 | Rappaport et al. |
| 9,262,587 | B2 | 2/2016 | Barr et al. |
| 9,572,682 | B2 * | 2/2017 | Aghazadeh ............... A61F 2/46 |
| 2004/0130572 | A1 * | 7/2004 | Bala ...................... G06F 9/4446 715/762 |
| 2008/0056552 | A1 | 3/2008 | Muller |
| 2008/0255442 | A1 * | 10/2008 | Ashby .................... A61B 5/103 600/407 |
| 2008/0269596 | A1 | 10/2008 | Revie et al. |
| 2011/0157029 | A1 * | 6/2011 | Tseng .................. G06F 3/04883 345/173 |
| 2011/0166435 | A1 * | 7/2011 | Lye ........................ A61B 19/22 600/407 |
| 2011/0238431 | A1 | 9/2011 | Cionni et al. |
| 2011/0320153 | A1 | 12/2011 | Lightcap et al. |
| 2012/0310075 | A1 * | 12/2012 | Russell ................ A61B 5/1071 600/407 |
| 2013/0072787 | A1 * | 3/2013 | Wallace ................... A61B 6/12 600/424 |
| 2013/0158439 | A1 * | 6/2013 | Clarke ..................... A61B 5/11 600/595 |
| 2013/0235071 | A1 * | 9/2013 | Ubillos ................. G06F 3/0484 345/600 |
| 2013/0304429 | A1 | 11/2013 | Haimerl |
| 2014/0378828 | A1 * | 12/2014 | Penenberg ............. A61B 34/25 600/424 |
| 2015/0146946 | A1 | 5/2015 | Elhawary |

OTHER PUBLICATIONS

Kilicoglu et al., "Cementless Total Hip Arthoplasty With Modified Oblique Femoral Shortening Osteotomy in Crowe Type IV Congenital Hip Dislocation", The Journal of Arthoplasty vol. 28 No. 1 2013.*

Lazennec et al., "Pelvis and total hip arthroplasty acetabular component orientations in sitting and standing positions: Measurements reproductibility with EOS imaging system versus conventional radiographies" Orthopaedics & Traumatology: Surgery & Research (2011) 97, 373-380.*

Smith & Nephew, AchieveCAS Computer Assisted Surgery, Surgical Technique, Total Hip Arthroplasty. 2006 (retrieved Nov. 26, 2017 from <http://www.smith-nephew.com/global/assets/pdf/products/surgical/cas_hip_st_low.pdf>).*

Le Huec et al., "Pelvic parameters: origin and significance" European Spine Journal. vol. 20, supplement 5, Sep. 2011.*

Gross et al., "Intraoperative Radiographs for Placing Acetabular Components in Hip Resurfacing Arthroplasty" Clin Orthop Relat Res (2011) 469:1554-1559.*

Ezzet et al., "Use of Intraoperative X-rays to Optimize Component Position and Leg Length During Total Hip Arthroplasty" Journal of Arthroplasty, vol. 29, Issue 3, Mar. 2014, pp. 580-585, available online Sep. 2013 (Year: 2013).*

Voyant Health, TraumaCad User's Guide, 2010 (Year: 2010).*

Park et al., "Are Portable Imaging Intraoperative Radiographs Helpful for Assessing Adequate Acetabular Cup Positioning in Total Hip Arthroplasty?" J Korean Med Sci 2009; 24:315-319 (Year: 2009).*

International Patent Application No. PCT/US2016/032172; Int'l Written Opinion and Search Report; dated Aug. 18. 2016; 6 pages.

U.S. Appl. No. 14/481,810; Third-Party Submission; Sep. 28, 2016; 11 pages.

Kojima et al.; "Morphological characteristics of the bony birth canal in patients with developmental dysplasia of the hip (DDH): investigation by three-dimensional CT"; J. Ortho Sci.; vol. 6; 2001; p. 217-222.

Tannast et al.; "Estimation of pelvic tilt on anteroposterior X-rays—a comparison of six parameters"; Skeletal Radiol; vol. 35; 2006; p. 149-155.

* cited by examiner

US 10,743,945 B2

SURGICAL METHOD AND WORKFLOW

CROSS-REFERENCE TO RELATED APPLICATIONS

This application is a continuation-in-part of U.S. application Ser. No. 14/481,810, filed Sep. 9, 2014, which is a continuation-in-part of U.S. application Ser. No. 13/633,799, filed Oct. 2, 2012 and issued as U.S. Pat. No. 8,831,324. The current application is based upon the identical specification (with minor spelling corrections) as the parent '799 patent application. The originally filed claims of the parent '799 patent application are incorporated by reference.

TECHNICAL FIELD

This invention relates to a surgical method and a workflow or protocol to make a surgical procedure more efficient using digital radiographic imaging.

BACKGROUND

In conducting certain surgical procedures, such as total hip arthroplasty ("THA"), the surgeon relies on radiographic images to help guide the proper placement of the prosthesis. Unfortunately, even with current technology, any surgeon is likely to admit that a quality intraoperative X-ray cannot be achieved. Trying to get a quality X-ray of a patient can be time consuming and exposes the patient to more radiation than desirable. The surgeon has to wait as the film is taken to another location for processing and brought back for review. If there are any problems with the film, the X-ray must be taken again. As such, there is no convenient intraoperative technique available for achieving perfect prosthesis placement every time.

For the foregoing reasons there is a need for a system that allows the surgeon to acquire a high-quality radiographic image that can be processed in the operating room so as to minimize the overall surgical procedure time and potential excess radiation exposure.

SUMMARY

The present invention is directed to a method and system that improves the efficiency and effectiveness of a surgical procedure, such as total hip arthroplasty. The method comprises acquiring a digital radiographic image of a patient, processing the radiographic image through a checklist, and making necessary adjustments to the patient or prosthetic based on processed information with minimal interruption in the surgical procedure.

The surgeon can walk through a workflow of choice to guide him through each step of the surgical procedure selected. The workflow can guide the surgeon through estimated component placement and a checklist of items to consider during the surgery. For example, in estimating component placement, the system can identify standard bone preparation tools, approximate broach size and judge anteversion for the femur, determine standard acetabular placement with screw and trial liner, determine limb length and offset estimates, determine a trial range of motion, and obtain anteroposterior and posteroanterior radiographic images. In working through the checklist, the surgeon can reconcile right/left and contrasts, reconcile pelvic rotation using trans-ischial line and mid-sacral line, reconcile tilt, read all parameters, make adjustments as indicated, and repeat any films necessary.

DETAILED DESCRIPTION OF THE INVENTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

The present invention is a system and method for a surgical workflow. It allows radiographic images, such as X-ray images, to be acquired and displayed in digital form on a host computer for immediate review. Quality intraoperative X-ray images cannot be achieved with current technology. With the present system, however, high-quality digital radiographic images can be acquired quickly. The digital images can also be archived or forwarded to other medical personnel for further evaluation as required. With immediate acquisition of a high quality radiographic image, the surgeon is able to make the necessary adjustment on the patient or a prosthetic to perform the surgery in a more efficient manner.

Image Acquisition

Figure 1:
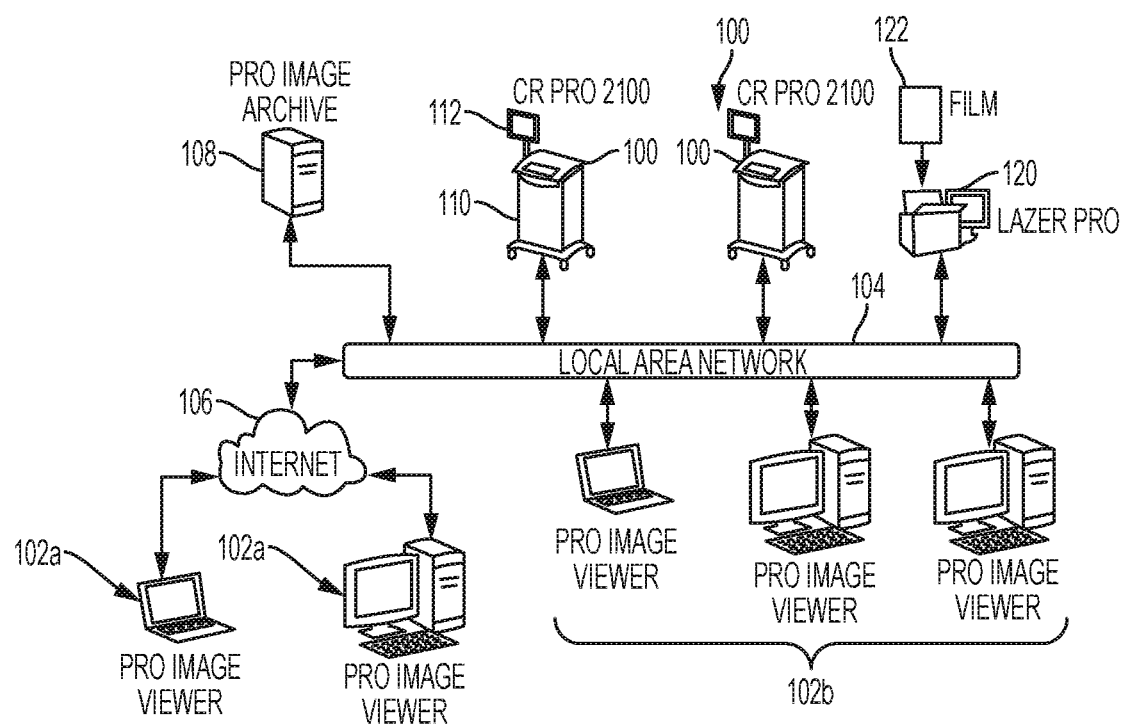
FIG. 1 shows an embodiment of the computer architecture of the present invention.
Figure 2:
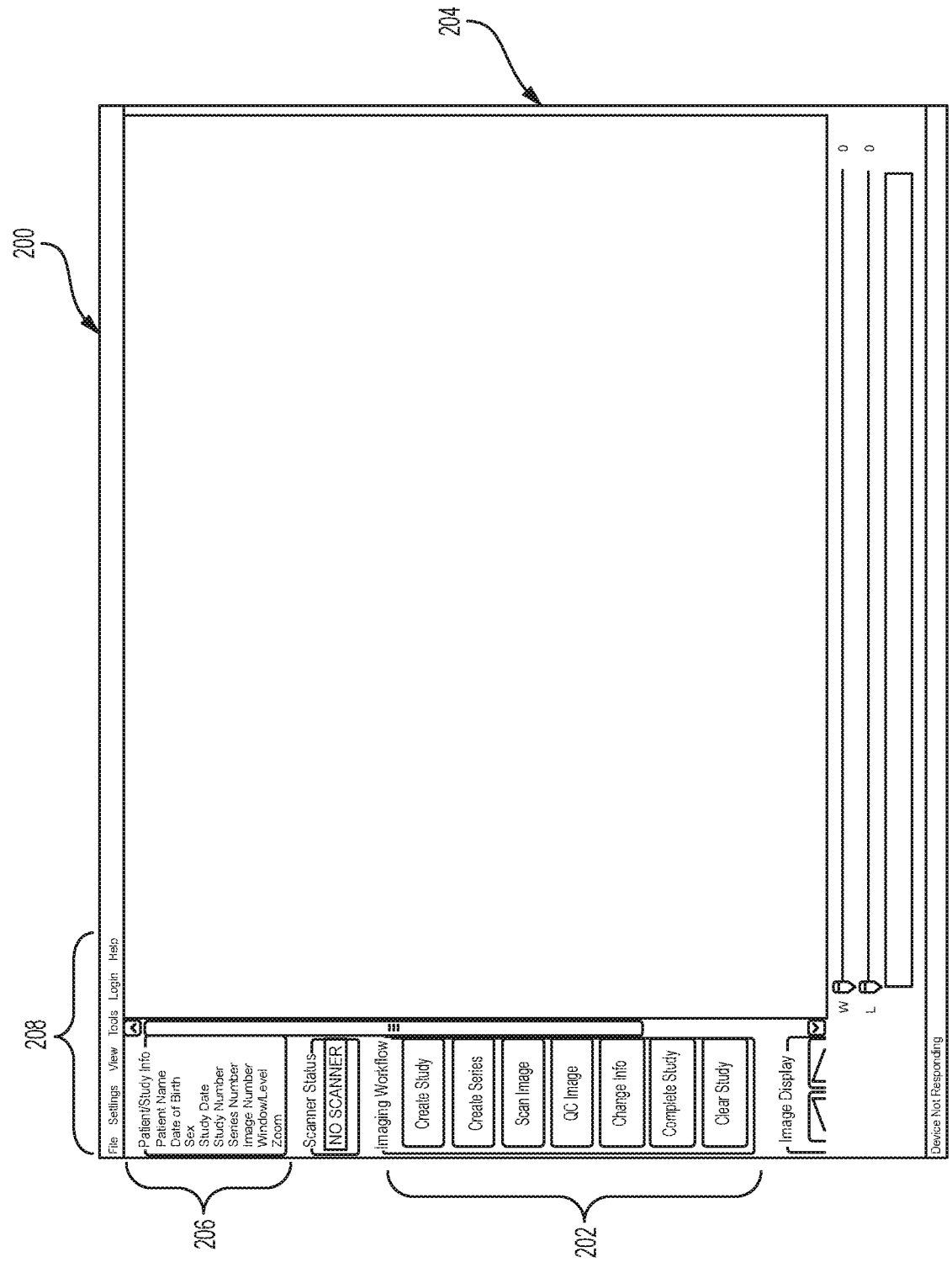
FIG. 2 shows an embodiment of an image frame.

Digital radiographic images can be acquired via digital radiography or computed radiography. For example, as shown in FIG. 1, in computed radiography, a radiological device 100 scans erasable phosphor plates exposed to X-rays and transmits the images to an imaging onboard computer 110 (either through a wired or wireless connection) for review, archiving, or forwarding to other facilities 102a, 102b through a local area network 104 and/or through the Internet 106 for further evaluation and/or archiving 108. In some embodiments, a scanner 120 may scan existing X-ray files 122 and convert them to digital radiographic images. Acquired images can be saved in a variety of formats, such as tiff, jpeg, png, bmp, dicom, and raw formatted images for both reading and writing.

Digital radiography offers numerous advantages over traditional X-ray methods. For example, digital radiography generates low radiation levels, specifically, below levels required by traditional X-ray machines to capture a detailed image on radiographic film 122. In addition, a radiographic image 500 can be viewed much quicker than with traditional X-ray film due to the reduced image acquisition time. Therefore, overall exposure to radiation is reduced due to the lower levels and shorter exposure times.

As shown in FIGS. 2-8, once a digital radiographic image 500 has been acquired, the radiographic image 500 can be processed and optimized by a computer 110, or any other computing device, such as a tablet, a smart phone, and the like. The computer 110 will display on a display device 112 (such as a monitor, television, screen, tablet, etc.) a main screen or main window 200 providing workflow action buttons 202, an image frame 204 to display the radiographic image 500, an information frame 206 displaying the information associated with the radiographic image displayed, and typical menu items 208.

Figure 3:
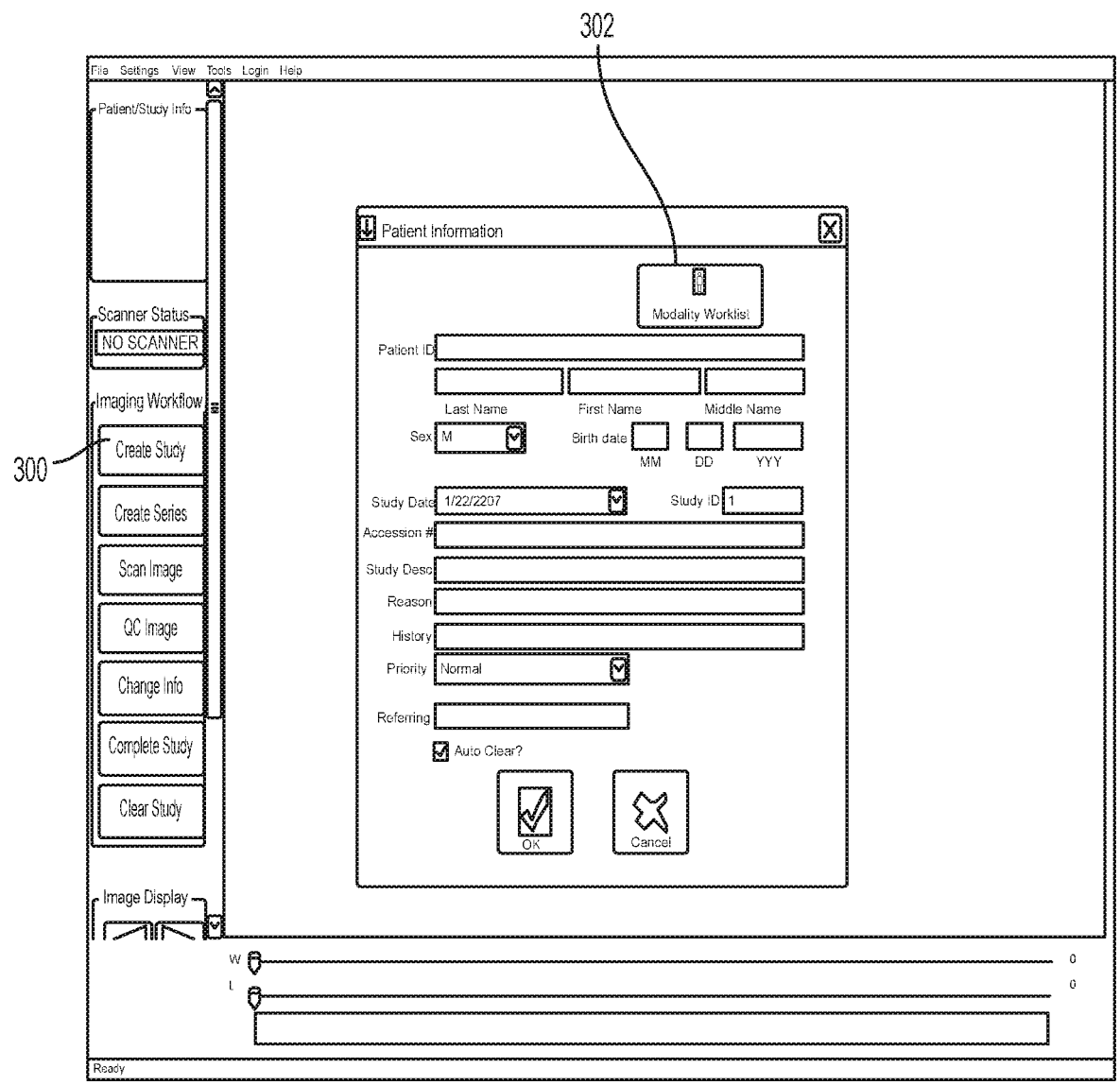
FIG. 3 shows an embodiment of a patient information window.

The workflow 202 steps may comprise creating a study, creating a series, scanning an image, performing quality control on the image, changing information, completing the study, and clearing the study. Creating a study begins with entering information related to the patient, the patient's medical condition, a recommended medical procedure, and any other information relevant to the patient and the condition being treated or diagnosed. As shown in FIG. 3, a create study button 300 can be provided to begin this process. A patient information window 302 may be provided with various fillable fields to input the relevant information. Once a study is created, an acquired radiographic image 500 can be uploaded and saved to that study.

Figure 4:
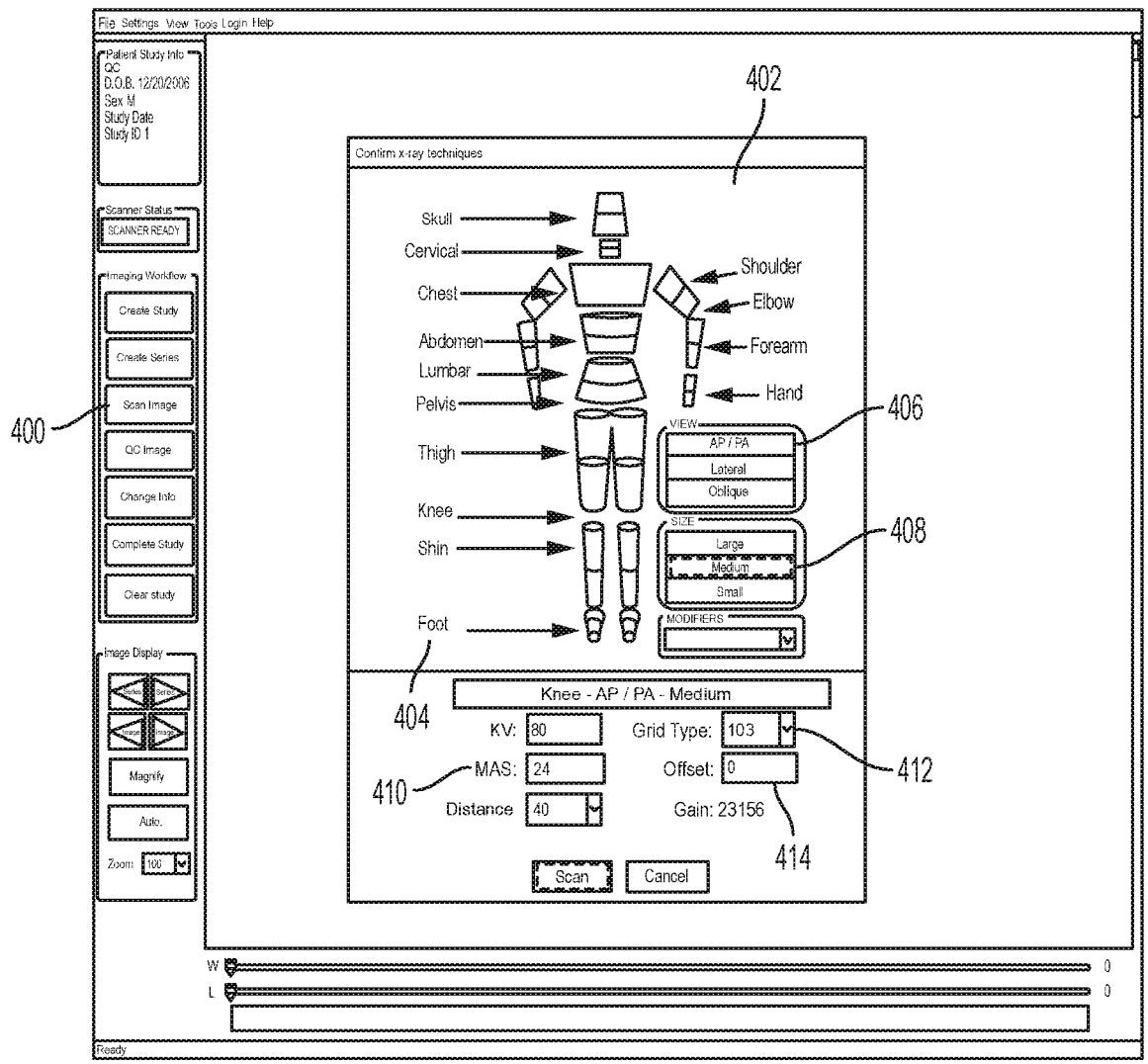
FIG. 4 shows an embodiment of a scanning window.
Figure 5:
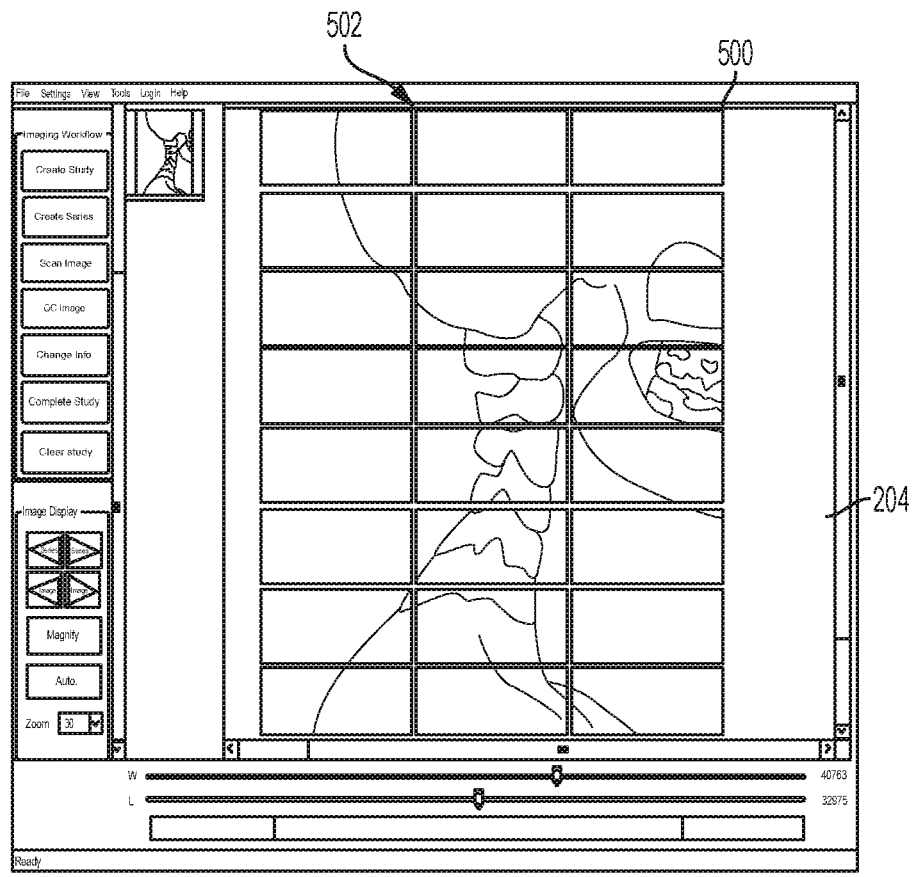
FIG. 5 shows an embodiment of a digital radiographic image being acquired.

Scanning an image allows the user to acquire a radiographic image of a particular body part for processing. As shown in FIG. 4, a scan image button 400 may be provided, actuation of which opens a scanning window 402 that allows the user to select such configurations as a particular body part or region 404 to be scanned, the view of the scan 406, the patient's size 408, the particular technique used 410, the grid type 412, the offset 414, and the like. Selecting a body part may involve selecting the corresponding body part of an image displayed on the image frame, or selecting the body part from a list of body parts. Once the scan is initiated, the images may be displayed line by line in the image frame 204 as it is being scanned as shown in FIG. 5. In some embodiments, a grid 502 may be provided. Using the grid 502, the image orientation can be verified and adjusted. For example, the image 500 can be rotated by any degree, then flipped, inverted, or otherwise adjusted, and processed further as discussed below.

Figure 6:
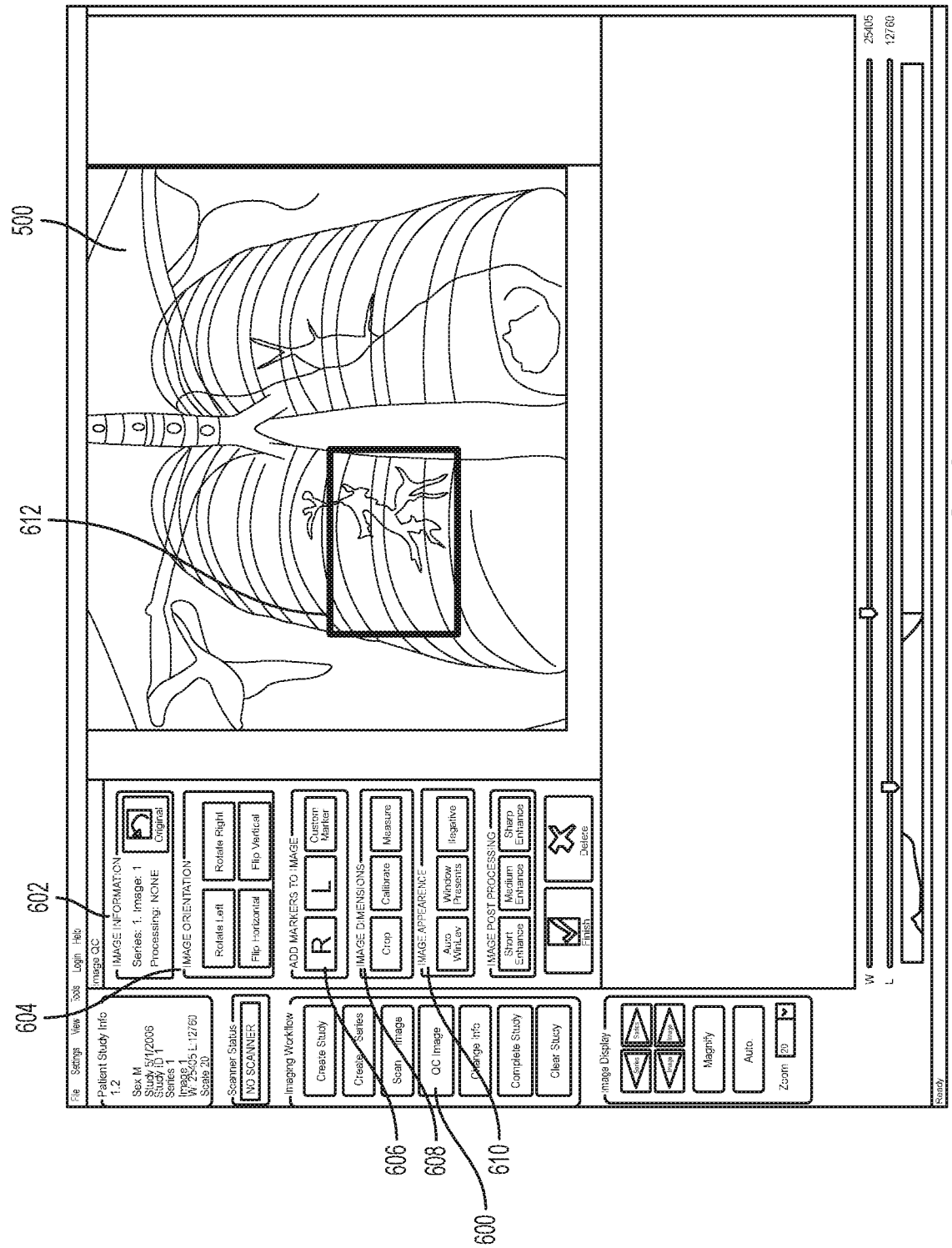
FIG. 6 shows an embodiment of an image quality check window.

Once the image 500 has been acquired, the user can perform a quality control (QC) check on the image. As shown in FIG. 6, a layout template or a QC image button 600 may be provided, actuation of which opens an image QC window 602 providing a number of features to improve the quality and layout of the radiographic image 500 acquired. For example, the image QC window 602 may provide features to orient the image 604, add markers 606 to the image, annotate the image, change the image dimensions and take measurements or sizing on the image 608, change the appearance of the image 610, and the like.

Therefore, using the image QC window 602, the user can process, modify, and interact with the image 500, such as rotating to the left, rotating to the right, flipping horizontally, flipping vertically, cropping, zooming, magnifying, moving or panning the image, changing the window width, inverting the image to a negative image, adjusting the level (brightness and contrast) of the image, adding or creating markers to indicate various information about the image, adding measuring lines to determine lengths, distances, angles, and the like. Additional features can be added, and any feature can be removed and added back again so as to configure the layout template according to the user's needs.

Figure 7:
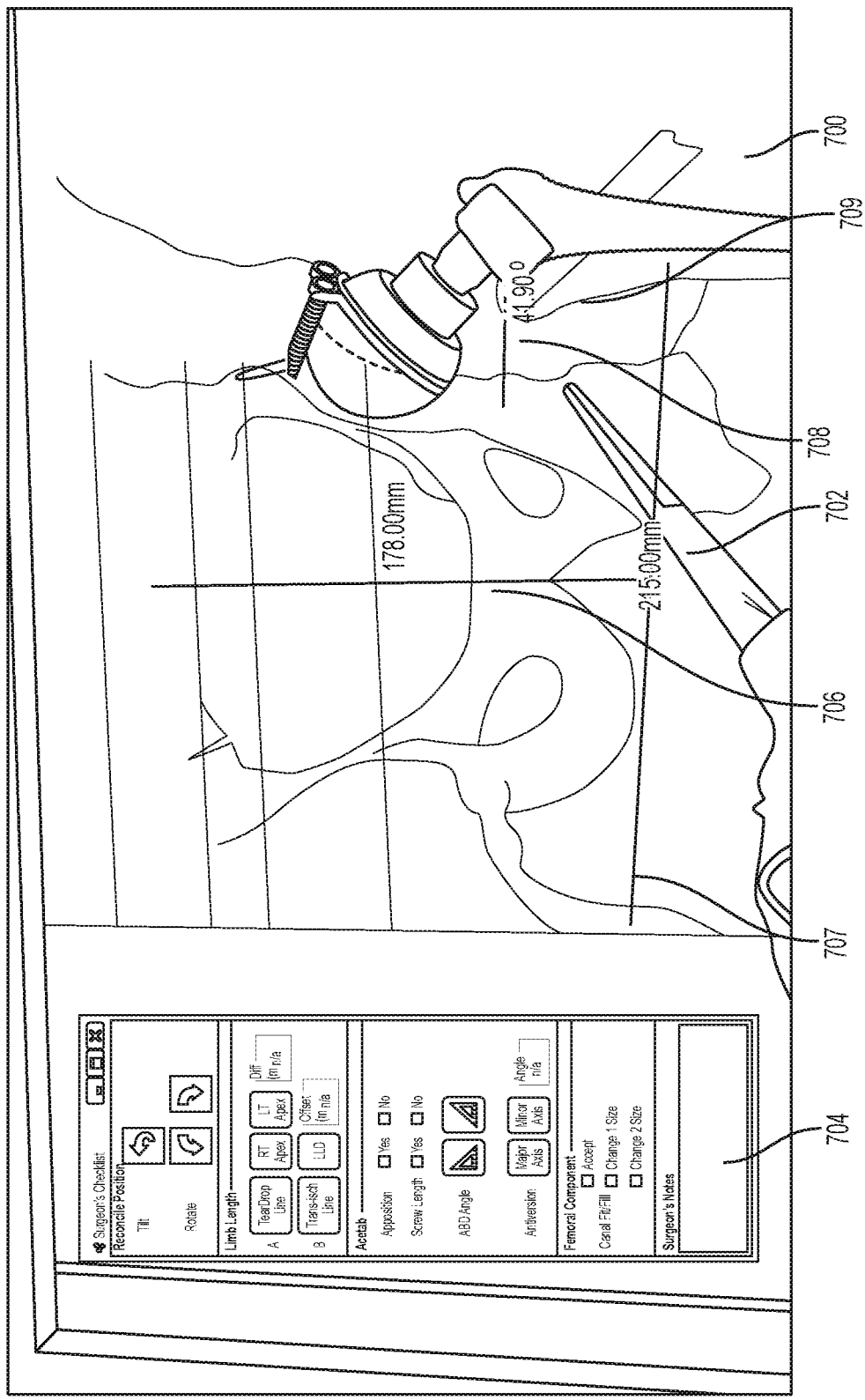
FIG. 7 shows an embodiment of an image displayed on a touchscreen for processing.

In some embodiments, processing, modifying, and interacting with the image 500 can be done on the image frame 204 instead of with the image QC window 602. For example, the display device 110 showing the radiographic image 500 may be a touchscreen device 700 as shown in FIG. 7. The user may use his fingers or a pointing device or any tool 702 to make gestures on a touchscreen 700 to effectuate the desired feature and view parameters that would assist the surgeon during the surgical procedure. For example, if a scanned image 500 is not properly aligned in the image frame 204, the user may tap or double tap the touchscreen 700 on the scanned image 500 and cause it to automatically rotate into the proper orientation. Gridlines 502 may be displayed on the image frame 204 as a guide for proper alignment. Alternatively, the user can place one or more fingers on the image frame 204 and make a rotating gesture to cause image 500 to rotate in the direction of the gesture. In some embodiments, the user may input specific values as the precise measurement for modification. For example, the user may indicate that the radiographic image 500 is to be rotated by a specified angle of rotation.

Taking measurements can be done in a similar fashion. Actuation of any of the features in the image QC window 602 may open a tools window 704 containing a checklist with electronic tools that are specific for the feature actuated. For example, if a measurement button is actuated, a tools window 704 may be displayed with a set of electronic tools that can be actuated to take measurements on the radiographic image. Actuating a length tool may allow the user to draw lines 706 on the radiographic image 500 which represents a length on the image 500. Actuating an angle tool allows the user to draw angles 708 and adjust the angle 708 drawn so that the user can measure the angle between structures shown on the radiographic image 500. Using the touchscreen 700, the user is able to move the lines 706 or angles 708 to various positions on the radiographic image 500 to take the measurement of various structures on the radiographic image. Lines 706 and angles 708 already drawn can be modified to change the length and/or angles. New lines and angles can also be created to measure multiple structures.

Based on measurements determined on the radiographic image 500, the surgeon or other medical personnel can make adjustments during the surgical procedure, such as adjusting the position of the patient, the patient's body part, a prosthetic, a surgical tool, and the like to achieve a desired position, thereby eliminating any delay and interruption during the surgical procedure.

By way of example only, as shown in FIG. 7, a radiographic image of the hip area is displayed on a touchscreen 706 along with the surgeon's checklist 704 to allow the surgeon to check desired parameters to assure the surgical procedure will be performed efficiently and accurately. Based on the acquired image, the surgeon can make sure the left and right sides of the image are properly displayed and the contrast adjusted. The surgeon may touch a point on the mid sacrum. This displays a vertical line 706 which can be used to determine the presence of pelvic tilt. Significant tilt or rotation of the pelvis would render subsequent measurements inaccurate. If this line 706, starting at mid sacrum passes to one side of the symphysis pubis by more than, for example, a centimeter, then the patient's position should be adjusted so that the line 706 is as close to mid symphysis as possible to reconcile pelvic tilt.

Next, the surgeon may actuate a horizontal line tool to draw either a trans-ischial or trans-ischial tuberosity line 707 to reconcile pelvic rotation. This identifies a horizontal axis orientation in relation to the pelvis. This line 707 creates, for example, a reference for subsequent angular and linear limb length and offset measurements.

The surgeon may then actuate an angle tool from the checklist 704 to display an acetabular abduction angle 708, for example, at 45 degrees. This 45 degree angle is referenced to the previously drawn horizontal (teardrop or trans-ischial) line 707 representing the transverse pelvic axis.

The surgeon may actuate a measure offset tool from the checklist 704 to display a measuring line 709. In this example, the measuring line 709 is displayed as a line parallel to horizontal 707. The measuring line 709 can be set to start at any predetermined length, for example, the measured amount on the pre-op X-ray. This is, generally speaking, the amount of lateralization of the femur in relation to the pelvis, which is as important as limb length in THA.

With the measuring line 709, major and minor diameters of acetabular component can be determined. These numbers feed into a calculation of "acetabular anteversion," another important parameter in THA.

Actuation of an annotation tool permits annotation of accuracy of femoral component sizing. All annotations can be saved as part of the patient's medical record. Once the combination of these steps are complete, the surgeon is in a much better position to accurately place the acetabular component and assure that the location of the screws is acceptable. By performing this combination of steps from the checklist and getting immediate results during the actual surgical procedure, the surgeon is able to perform the surgery more accurately and quicker than without the checklist. Other parameters to be checked may be determined by the surgeon as needed.

Specific regions of interest can also be isolated and that region of interest modified in the ways described above. For example, the user can click on the image 500 and create a box 612 around the region of interest to display a blow-up of the region of interest.

Figure 8:
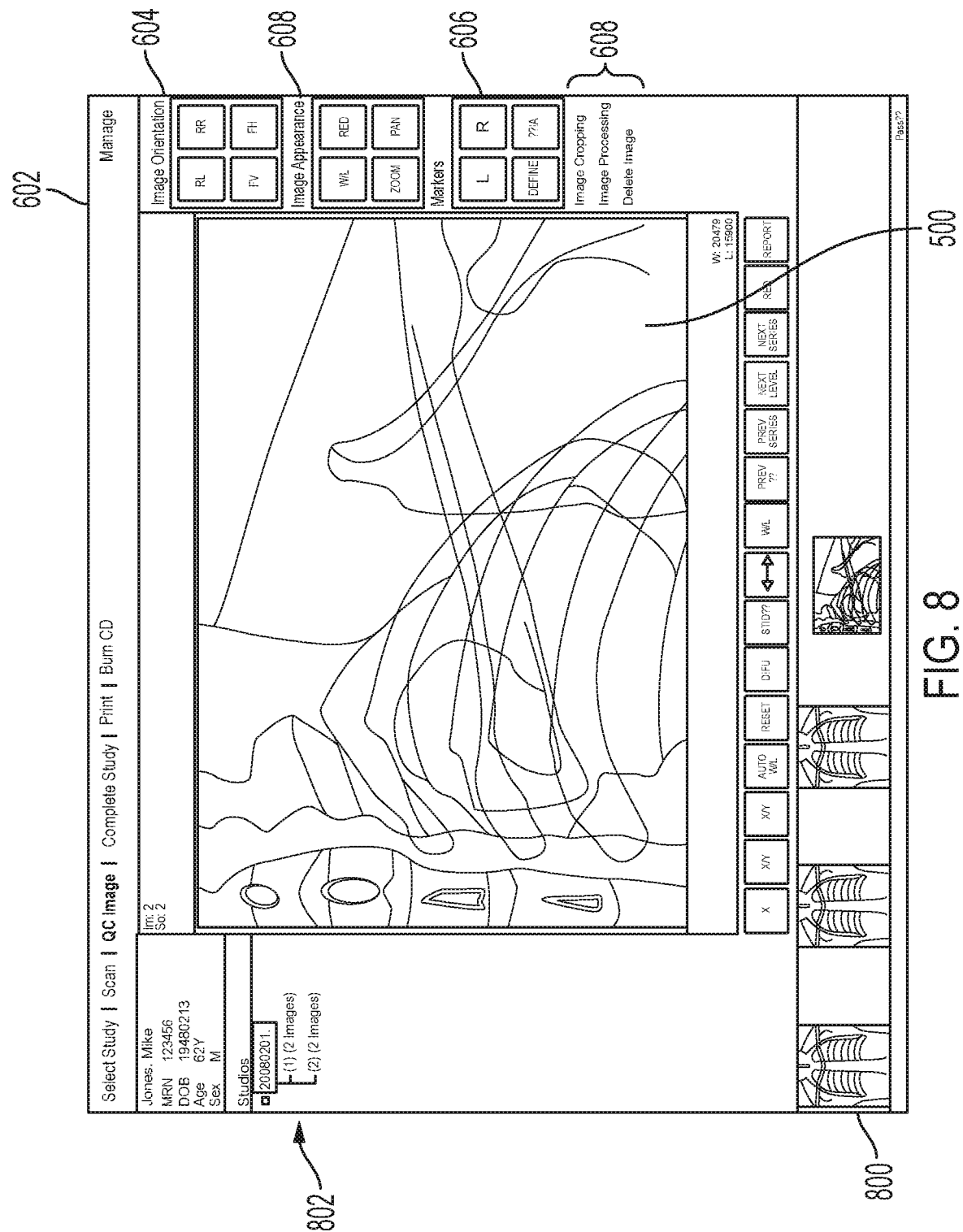
FIG. 8 shows another embodiment of an image frame of a series of a study.

Multiple images may be acquired and saved as a series of a study. Selected images can be displayed together or individually in the image frame 204. All images in the series may be provided as thumbnail images 800 adjacent to the image frame 204 to show all images related to the image 500 displayed in the image frame 204 as shown in FIG. 8.

Once the image 500 has been acquired, before, during, or after any processing, the system can provide a checklist of parameters for the user to review and indicate whether the necessary steps have been performed. The checklist can include, but is not limited to, the following items or parameters: orientation of the radiographic image, component orientation, cup apposition (in-growth), cup anteversion angle, cup abduction angle, screw positions, femoral sizing, femoral component alignment, limb length, and offset between the first edge of a bone and a second edge of the bone.

Additional buttons may be provided to delete the image, save the image, clear the image, undo an action, redo an action, and the like. Each of these steps can be done during the operation without the surgeon having to leave his patient.

Saved files can be opened in the typical manner from a database or directory 802. The system may display a worklist window for the user to view and select study from a worklist. The worklist may be organized by a specific filter, such as name, date, medical condition, and the like. Selection of a specific filter displays all studies categorized under that filter. Each study may have additional information associated with it. The list of studies may be sortable based on any of the additional information. Selection of a study displays an image window that allows the surgeon to review acquired digital radiographic images.

Any created study can be transmitted to another computer 102a, 102b via a local area network 104 and/or the Internet 106, saved to a hard drive or saved to any other type of non-transitory computer readable medium, such as a CD, DVD, USB drive, and the like.

Additional workflow states include the state of arrival of a study, a verification state to indicate that a study is complete and accurate, a dictated state to indicate a report for a study has been dictated, a transcribed state to indicate that a report has been transcribed, and a finalized state to indicate that a report has been approved and finalized.

This system allows the user to take an X-ray before and during the middle of an operation and make the necessary adjustments immediately upon acquiring the results to greatly improve the accuracy of the surgical procedure. In addition, the accuracy resulting from each step synergistically improves the accuracy of any subsequent step and, therefore, significantly improves the outcome of the total surgical procedure in a way that cannot be achieved by improving the accuracy of any one step alone.

Figure 9:
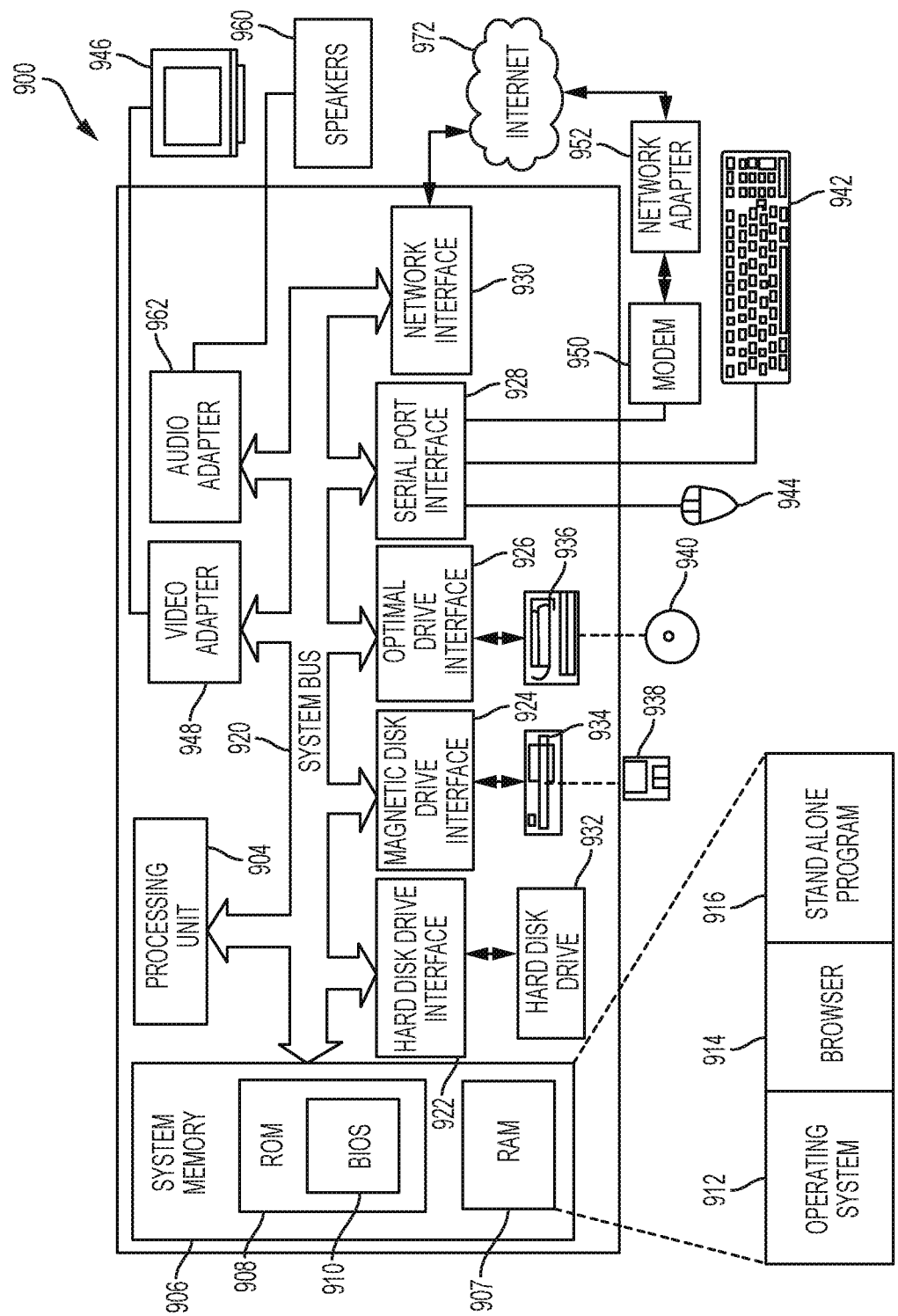
FIG. 9 shows an embodiment of a computer architecture embodying the present invention.

FIG. 9 depicts exemplary hardware for a surgical method and workflow system for providing efficient acquisition and processing of radiographic images for surgery. The system may be in the form of a computer 900 that includes a processing unit 904, a system memory 904, and a system bus 920 that operatively couples various system components, including the system memory 906 to the processing unit 904. There may be only one or there may be more than one processing unit 904, such that the processor of computer 900 comprises a single central processing unit (CPU), or a plurality of processing units, commonly referred to as a parallel processing environment. The computer 900 may be a conventional computer, a distributed computer, a web server, a file server, a tablet or iPad, a smart phone, or any other type of computing device.

The system bus 920 may be any of several types of bus structures including a memory bus or memory controller, a peripheral bus, a switched fabric, point-to-point connections, and a local bus using any of a variety of bus architectures. The system memory 906 may also be referred to as simply the memory, and includes read only memory (ROM) 908 and random access memory (RAM) 907. A basic input/output system (BIOS) 910, containing the basic routines that help to transfer information between elements within the computer 900, such as during start-up, is stored in ROM 908. The computer 900 may further include a hard disk drive 932 for reading from and writing to a hard disk, not shown, a magnetic disk drive 934 for reading from or writing to a removable magnetic disk 938, and/or an optical disk drive 936 for reading from or writing to a removable optical disk 940 such as a CD-ROM or other optical media.

The hard disk drive 932, magnetic disk drive 934, and optical disk drive 936 may be connected to the system bus 920 by a hard disk drive interface 922, a magnetic disk drive interface 924, and an optical disk drive interface 926, respectively. The drives and their associated computer-readable media provide nonvolatile storage of computer-readable instructions; data structures, e.g., a catalog and a context-based index; program modules, e.g., a web service and an indexing robot; and other data for the computer 900. It should be appreciated by those skilled in the art that any type of computer-readable media that can store data that is accessible by a computer, for example, magnetic cassettes, flash memory cards, USB drives, digital video disks, RAM, and ROM, may be used in the exemplary operating environment.

A number of program modules may be stored on the hard disk 932, magnetic disk 934, optical disk 936, ROM 908, or RAM 907, including an operating system 912, browser 914, stand alone program 916, etc. A user may enter commands and information into the personal computer 900 through input devices such as a keyboard 942 and a pointing device 944, for example, a mouse. Other input devices (not shown) may include, for example, a microphone, a joystick, a game pad, a tablet, a touch screen device, a satellite dish, a scanner, a facsimile machine, and a video camera. These and other input devices are often connected to the processing unit 904 through a serial port interface 928 that is coupled to the system bus 920, but may be connected by other interfaces, such as a parallel port, game port or a universal serial bus (USB).

A monitor 946 or other type of display device is also connected to the system bus 920 via an interface, such as a video adapter 948. In addition to the monitor 946, computers typically include other peripheral output devices, such as speakers 960 connected to the system bus 920 via an audio adapter 962, and printers. These and other output devices are often connected to the processing unit 904 through the serial port interface 928 that is coupled to the system bus 920, but may be connected by other interfaces, such as a parallel port, game port, or a universal serial bus (USB).

The computer 900 may operate in a networked environment using logical connections to one or more remote computers. These logical connections may be achieved by a communication device coupled to or integral with the computer 900; the application is not limited to a particular type of communications device. The remote computer may be another computer, a server, a router, a network personal computer, a client, a peer device, or other common network node, and typically includes many or all of the elements described above relative to the computer 900, although only a memory storage device has been illustrated in FIG. 9. The computer 900 can be logically connected to the Internet 972. The logical connection can include a local area network (LAN), wide area network (WAN), personal area network (PAN), campus area network (CAN), metropolitan area network (MAN), or global area network (GAN). Such networking environments are commonplace in office networks, enterprise-wide computer networks, intranets and the Internet, which are all types of networks.

When used in a LAN environment, the computer 900 may be connected to the local network through a network interface or adapter 930, which is one type of communications device. When used in a WAN environment, the computer 900 typically includes a modem 950, a network adapter 952, or any other type of communications device for establishing communications over the wide area network. The modem 950, which may be internal or external, is connected to the system bus 920 via the serial port interface 928. In a networked environment, program modules depicted relative to the personal computer 900, or portions thereof, may be stored in a remote memory storage device. It is appreciated that the network connections shown are exemplary and other means of, and communications devices for, establishing a communications link between the computers may be used.

The system can take the form of a computer program product 916 accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The medium can be an apparatus or device that utilizes or implements electronic, magnetic, optical, electromagnetic, infrared signal or other propagation medium, or semiconductor system. Examples of a computer-readable medium comprise a semiconductor or solid-state memory, magnetic tape, a removable computer diskette, a random access memory, a read-only memory, a rigid magnetic disk and an optical disk. Current examples of optical disks comprise compact disk-read only memory (CD-ROM), compact disk-read/write (CD-R/W) and DVD formats.

A data processing system suitable for storing and/or executing program code comprises at least one processor coupled directly or indirectly to memory elements through a system bus. The memory elements can include local memory employed during actual execution of the program code, bulk storage, and cache memory that provide temporary storage of at least some program code in order to reduce the number of times code is retrieved from bulk storage during execution.

Input/output or I/O devices (including, but not limited to, keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modems and Ethernet cards are just a few of the currently available types of network adapters.

Furthermore, computers and other related electronic devices can be remotely connected to either the LANs or the WAN via a digital communications device, modem and temporary telephone, or a wireless link. It will be appreciated that the Internet comprises a vast number of such interconnected networks, computers, and routers.

The foregoing description of the preferred embodiment of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

What is claimed is:

1. A method of intraoperative imaging comprising steps of:
providing a computerized surgical workflow program to a computer device, the surgical workflow program guiding a user through steps of a surgical procedure;
receiving through the computer device, from the user, as part of a surgical workflow offered by the surgical workflow program, activation of a graphical tool for performing intraoperative measurements;
receiving an intraoperative radiographic image data pertaining to a patient and pertaining to a first surgical placement of a prosthetic implant during a surgery;
displaying a visual representation of the intraoperative radiographic image data on an electronic display of the computer device;
providing a graphical interface to the user on the electronic display that allows the user to mark an anatomical structure on the visual representation of the radiographic image data on the electronic display;

upon receipt of the user marking the anatomical structure on the visual representation of the radiographic image data, superimposing at least one of (a) a measuring line and (b) a measuring angle onto the displayed visual representation of the radiographic image data on the electronic display, wherein, in response to the anatomical structure marked, the measuring line or the measuring angle are automatically drawn by the surgical workflow program with a specific set of parameters; and displaying to the user on the electronic display measurement information associated with the at least one of (a) the measuring line and (b) the measuring angle onto the displayed visual representation of the radiographic image data;

wherein the displayed measurement information pertains to a surgical adjustment for the surgery with respect to at least one of: (i) the prosthetic implant, and (ii) anatomical components of the patient associated with the prosthetic implant; and repeating steps of receiving a subsequent intraoperative radiographic image data pertaining to the patient and pertaining to a subsequent surgical placement of the prosthetic implant during the surgery, displaying visual representations of the subsequent intraoperative radiographic image data on the electronic display of the computer device, and providing the graphical interface to the user on the electronic display to mark the visual representation of the subsequent radiographic image data on the electronic display until a desired placement of the prosthetic implant is achieved.

2. The method of claim 1, wherein the electronic display is a touchscreen display and receipt of the user marking the anatomical structure on the visual representation of the radiographic image data is through the touchscreen display.

3. The method of claim 2, further comprising steps of:
modifying at least one of (a) the measuring line and (b) the measuring angle upon receipt of a manipulation of the touchscreen display by the user; and
displaying to the user on the electronic display measurement information associated with at least one of the modified measuring line and the modified measuring angle.

4. The method of claim 2, further comprising steps of:
moving at least one of (a) the measuring line and (b) the measuring angle upon receipt of a manipulation of the touchscreen display by the user; and
displaying to the user on the electronic display measurement information associated with the movement of the at least one of (a) the measuring line and (b) the measuring angle.

5. The method of claim 2, further comprising a step of reorienting the visual representation of the radiographic image data on the electronic display upon receipt of a manipulation of the touchscreen display by the user.

6. The method of claim 5, wherein the reorienting is taken from a group consisting of:
rotating the visual representation of the radiographic image data on the electronic display;
flipping the visual representation of the radiographic image data on the electronic display;
inverting the visual representation of the radiographic image data on the electronic display; and
cropping the visual representation of the radiographic image data on the electronic display.

7. The method of claim 5, wherein the reorienting step includes a step of superimposing a grid image with the visual representation of the radiographic image data on the electronic display.

8. The method of claim 5, wherein the reorienting step includes the steps of:
receiving a user input value; and
reorienting the visual representation of the radiographic image data on the electronic display according to the user input value.

9. The method of claim 1, wherein the graphical tool is provided to the user as part of a checklist on the electronic display.

10. The method of claim 1, wherein the step of providing a graphical interface to the user on the electronic display that allows the user to mark the visual representation of the radiographic image data on the electronic display follows a selection, by the user, of the surgical workflow from a menu of several available surgical workflows.

11. The method of claim 10, wherein the graphical interface is provided to the user as part of a checklist on the electronic display associated with the selected surgical workflow.

12. The method of claim 1, further including steps of:
receiving annotation information from the user through a graphical annotation tool; and
saving the annotation information with a medical record associated with the patient.

13. The method of claim 1, wherein:
upon receipt of the user marking the anatomical structure on the visual representation of the radiographic image data, the superimposing step superimposes the measuring line onto the displayed visual representation of the radiographic image data on the electronic display; and
the displayed measurement information comprises length information associated with a length of the measuring line with respect to the displayed visual representation of the radiographic image data.

14. The method of claim 13, wherein:
upon receipt of the user marking the anatomical structure on the visual representation of the radiographic image data, the superimposing step superimposes the measuring line onto the displayed visual representation of the radiographic image data on the electronic display; and
the displaying step displays to the user on the electronic display angle information associated with an angle of the measuring line with respect to the displayed visual representation of the radiographic image data.

15. The method of claim 1, wherein:
upon receipt of the user marking the anatomical structure on the visual representation of the radiographic image data, the superimposing step superimposes the measuring line onto the displayed visual representation of the radiographic image data on the electronic display; and
the displayed measurement information comprises angle information associated with an angle of the measuring line with respect to the displayed visual representation of the radiographic image data.

16. The method of claim 15, wherein:
the radiographic image data pertains to a hip area of the patient and the prosthetic implant includes an acetabular cup component; and
the superimposing step superimposes an acetabular abduction angle of the acetabular cup component of the prosthetic implant onto the displayed visual representation of the radiographic image data on the electronic display.

17. The method of claim 1, further comprising: receiving length information from the user; and
wherein the displayed measurement information comprises the length information.

18. The method of claim 17, wherein the length information received from the user corresponds to an amount of lateralization of a femur of the patient in relation to a pelvis of the patient.

19. A method of intraoperative imaging, comprising steps of:
receiving intraoperative radiographic image data pertaining to a hip area of a patient and pertaining to a first surgical placement of a prosthetic hip implant during a surgery on a computerized device having a touchscreen display;
displaying a visual representation of the intraoperative radiographic image data on the touchscreen display of the computerized device;
upon receipt of a user touching a point corresponding to a mid sacrum of the hip area of the patient on the visual representation of the intraoperative radiographic image data on the touch-screen display superimposing a first measuring line onto the displayed visual representation of the intraoperative radiographic image data on the touchscreen display of the computerized device, wherein the measuring line starts at a location on the visual representation of the intraoperative radiographic image data associated with the mid sacrum of the hip area of the patient and passes a second location on the visual representation of the intraoperative radiographic image data associated with the hip area of the patient;
upon receipt of the user touching a second point corresponding to another area of the patient on the visual representation of the intraoperative radiographic image data on the touch-screen display superimposing a second measuring line onto the displayed visual representation of the intraoperative radiographic image data on the touchscreen display of the computerized device, wherein the second measuring line starts at a third location on the visual representation of the intraoperative radiographic image data and is automatically drawn with a predetermined length;
displaying to the user on the touchscreen display of the computerized device at least one of pelvic tilt and pelvic rotation information associated with the first or second measuring line onto the displayed visual representation of the intraoperative radiographic image data; and
repeating a step of receiving intraoperative radiographic image data pertaining to the patient and pertaining to a subsequent surgical placement of the prosthetic hip implant during the surgery.

20. The method of claim 19, further comprising a step of reorienting the visual representation of the intraoperative radiographic image data on the touchscreen display upon receipt of a manipulation of the touchscreen display by the user.

21. The method of claim 20, wherein the reorienting is taken from a group consisting of:
rotating the visual representation of the intraoperative radiographic image data on the touchscreen display;
flipping the visual representation of the intraoperative radiographic image data on the touchscreen display;
inverting the visual representation of the intraoperative radiographic image data on the touchscreen display; and
cropping the visual representation of the intraoperative radiographic image data on the touchscreen display.

22. The method of claim 20, wherein the reorienting step includes a step of superimposing a grid image with the visual representation of the intraoperative radiographic image data on the touchscreen display.

23. The method of claim 19, further comprising steps of:
receiving annotation information from the user through a graphical annotation tool; and
saving the annotation information with a medical record associated with the patient.

24. A method of intraoperative imaging comprising steps of:
providing a computerized surgical workflow program to a computer device, the surgical workflow program guiding a user through steps of a surgical procedure;
receiving an intraoperative radiographic image data pertaining to a patient and pertaining to a first surgical placement of a prosthetic implant during a surgery;
displaying a visual representation of the intraoperative radiographic image data on an electronic display of the computer device;
providing by the surgical workflow program a first graphical interface tool to the user on the electronic display that allows the user to mark the visual representation of the radiographic image data on the electronic display, and upon receipt of the user marking the visual representation of the radiographic image data, superimposing a reference line onto the displayed visual representation of the radiographic image data on the electronic display; and
providing by the surgical workflow program a second graphical interface tool to the user on the electronic display that superimposes a measuring line corresponding to the reference line onto the displayed visual representation of the radiographic image data on the electronic display, the measuring line having a predetermined parameter based upon receipt of a selection on the second graphical interface tool; and
displaying to the user on the electronic display measurement information associated with the measuring line corresponding to the reference line;
wherein the displayed measurement information pertains to a surgical adjustment for the surgery with respect to at least one of: (i) the prosthetic implant and (ii) anatomical components of the patient associated with the prosthetic implant;
receiving a second intraoperative radiographic image data pertaining to the patient and pertaining to an adjusted surgical placement of the prosthetic implant during the surgery;
displaying a visual representation of the second intraoperative radiographic image data on the electronic display of the computer device to confirm whether an adjustment of the patient and the adjusted surgical placement of the prosthetic fall within a desired range.

25. The method of claim 24, wherein the measurement information is angle information of the measuring line with respect to the reference line.

26. The method of claim 25, wherein:
the intraoperative radiographic image data is that of a hip area of the patient;
the reference line is at least one of a teardrop and trans-ischial tuberosity line; and the displayed measurement information comprises acetabular abduction angle information of the measuring line with respect to the reference line.

27. The method of claim 24, wherein the measurement information is offset information of the measuring line with respect to the reference line.

28. The method of claim 27, wherein:
the intraoperative radiographic image data is that of a hip area of the patient;
the reference line is at least one of a teardrop and trans-ischial tuberosity line; and
the displayed measurement information comprises an amount of lateralization of the femur in relation to the pelvis.

29. The method of claim 24, wherein said guiding the user through steps of the surgical procedure comprises providing a checklist of parameters for the user to review, the parameters comprising on or more taken from a group consisting of:
cup apposition information;
cup anteversion angle information;
screw position information;
femoral sizing information;
femoral component alignment;
limb length information; and
bone edge offset information.

* * * * *

UNITED STATES PATENT AND TRADEMARK OFFICE
CERTIFICATE OF CORRECTION

Page 1 of 1

PATENT NO. : 10,743,945 B2
APPLICATION NO. : 15/133999
DATED : August 18, 2020
INVENTOR(S) : Brad L. Penenberg It is certified that error appears in the above-identified patent and that said Letters Patent is hereby corrected as shown below:

On the Title Page

Item (72) inventors should be changed from:
-- Brad L. Penenberg, Los Angeles, CA (US) --

To:
-- Brad L. Penenberg, Los Angeles, CA (US); Wenchao Tao, Los Angeles, CA (US) --

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*